United States Patent
Sugimoto et al.

(10) Patent No.: US 11,867,694 B2
(45) Date of Patent: Jan. 9, 2024

(54) LATEX PARTICLES FOR MEASUREMENT REAGENTS, SENSITIZED LATEX PARTICLES, AND MEASUREMENT REAGENT FOR TURBIDIMETRIC IMMUNOASSAY

(71) Applicants: SEKISUI CHEMICAL CO., LTD., Osaka (JP); SEKISUI MEDICAL CO., LTD., Tokyo (JP)

(72) Inventors: Satoru Sugimoto, Mishima-gun (JP); Takeshi Wakiya, Mishima-gun (JP); Shinichiro Kitahara, Tokyo (JP); Maasa Yaji, Tokyo (JP); Yuya Inaba, Tokyo (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 716 days.

(21) Appl. No.: 16/616,371

(22) PCT Filed: May 24, 2018

(86) PCT No.: PCT/JP2018/020076
§ 371 (c)(1),
(2) Date: Nov. 22, 2019

(87) PCT Pub. No.: WO2018/216784
PCT Pub. Date: Nov. 29, 2018

(65) Prior Publication Data
US 2020/0080996 A1 Mar. 12, 2020

(30) Foreign Application Priority Data
May 24, 2017 (JP) .................................. 2017-103093

(51) Int. Cl.
*G01N 33/546* (2006.01)
*C08F 12/32* (2006.01)
(Continued)

(52) U.S. Cl.
CPC ............ *G01N 33/546* (2013.01); *C08F 12/08* (2013.01); *C08F 12/32* (2013.01); *C08F 22/20* (2013.01); *C08F 28/06* (2013.01)

(58) Field of Classification Search
None
See application file for complete search history.

(56) References Cited

U.S. PATENT DOCUMENTS

| 4,401,765 A | 8/1983 | Craig et al. |
| 4,921,915 A | 5/1990 | Dengler et al. |
| (Continued) | | |

FOREIGN PATENT DOCUMENTS

| CN | 103460046 A | 12/2013 |
| JP | 8-136547 A | 5/1969 |
| (Continued) | | |

OTHER PUBLICATIONS

English translation of Kuroda et al. (JP 08-136547) (Year: 1996).*
(Continued)

*Primary Examiner* — Ronak C Patel
(74) *Attorney, Agent, or Firm* — Birch, Stewart, Kolasch & Birch, LLP (57) ABSTRACT

The present invention relates to latex particles for measurement reagents, said latex particles having a coefficient of variation in particle diameters of 10% or less and an average particle diameter of 250 to 1000 nm. Each of the latex particles contains 20% by weight or more of a compound having a refractive index of 1.60 or more. The depth of a supernatant is 5 mm or less when a liquid dispersion having a solid matter concentration of 1% by weight, which is prepared by dispersing the latex particles in ultrapure water, is placed in a tubular 10-ml measuring cylinder having a body inner diameter of 10.8 mm and is then allowed to leave for 10 days. According to the particles, a measurement of a (Continued)

measurement sample can be performed at a high sensitivity even when the concentration of a substance to be tested in the measurement sample is low.

8 Claims, 1 Drawing Sheet

(51) Int. Cl.
*C08F 12/08* (2006.01)
*C08F 22/20* (2006.01)
*C08F 28/06* (2006.01)

(56) References Cited

U.S. PATENT DOCUMENTS

| | | | |
|---|---|---|---|
| 5,166,077 A | 11/1992 | Kihara et al. | |
| 2004/0171176 A1 | 9/2004 | Obana | |
| 2012/0196096 A1 | 8/2012 | Uematsu et al. | |
| 2014/0065726 A1* | 3/2014 | Kitahara | G01N 33/585 524/767 |
| 2015/0072147 A1* | 3/2015 | Brennan | C08J 9/18 521/63 |

FOREIGN PATENT DOCUMENTS

| | | | |
|---|---|---|---|
| JP | 58-47258 | A | 3/1983 |
| JP | 63-39909 | A | 2/1988 |
| JP | 63-273060 | A | 11/1988 |
| JP | 2001-296299 | A | 10/2001 |
| JP | 2008-215816 | A | 9/2008 |
| JP | 2012-177098 | A | 9/2012 |
| JP | 2012-201819 | A | 10/2012 |
| JP | 2013-210526 | A | 10/2013 |
| JP | 2015-65060 | A | 4/2015 |
| WO | WO 03/005031 | A1 | 1/2003 |
| WO | WO 2012/133771 | A1 | 10/2012 |
| WO | WO 2018-062557 | A1 | 4/2018 |

OTHER PUBLICATIONS

Office Action dated Nov. 24, 2021, in Japanese Patent Application No. 2019-520316.
International Search Report for PCT/JP2018/020076 (PCT/ISA/210) dated Aug. 28, 2018.
Written Opinion of the International Searching Authority for PCT/JP2018/020076 (PCT/ISA/237) dated Aug. 28, 2018.
English translation of International Preliminary Report on Patentability and Written Opinion dated Dec. 5, 2019, in PCT/JP2018/020076 (Forms PCT/IB/338, PCT/IB/373, and PCT/ISA/237).
Machine English translation of JP 2001-296299 (Oct. 26, 2001).
Machine English translation of JP 2008-215816 (Sep. 18, 2008).
Machine English translation of JP 2012-201819 (Oct. 22, 2012).
Machine English translation of JP 2013-210526 (Oct. 10, 2013).
Machine English translation of JP 2015-65060 (Apr. 9, 2015).
Machine English translation of JP 8-136547 (May 31, 1996).
Extended European Search Report dated Feb. 8, 2021, in European Patent Application No. 18805331.8.
English translation of the Chinese Office Action for Chinese Application No. 201880032945.8, dated Dec. 28, 2022.
Chinese Office Action and Search Report for Chinese Application No. 201880032945.8, dated Dec. 28, 2022, with an English translation.

* cited by examiner

LATEX PARTICLES FOR MEASUREMENT REAGENTS, SENSITIZED LATEX PARTICLES, AND MEASUREMENT REAGENT FOR TURBIDIMETRIC IMMUNOASSAY

TECHNICAL FIELD

The present invention relates to latex particles for measurement reagents that enable high-sensitivity measurement even when measuring a test sample containing a test substance at a dilute concentration. Further, the present invention relates to sensitized latex particles using the latex particles for measurement reagents, and a measurement reagent for turbidimetric immunoassay.

BACKGROUND ART

In a variety of fields including clinical laboratory tests, immunological measurement methods utilizing antigen-antibody reactions have been widely used as a method of quantitatively determining a trace test substance in a measurement reagent. Especially, a latex turbidimetric immunoassay using latex particles as a carrier for an antigen or an antibody is simply operated and takes a short period of time for measurement. Accordingly, there is a further increase in the kinds of trace test substances that employ the latex turbidimetric immunoassay as a measurement method.

Quantification of a test substance of an antigen, an antibody or the like in a test sample by the latex turbidimetric immunoassay is performed by optically detecting a change in the absorbance caused by aggregation of latex particles carrying the antigen or the antibody (hereinafter, also referred to as 'sensitized latex particles'). This change in the absorbance is on the basis of changes in apparent particle sizes of aggregates formed by the aggregation of the sensitized latex particles.

As the latex particles used as a carrier in the latex turbidimetric immunoassay, polystyrene-based latex particles containing polystyrene as a main component have been traditionally used because antigen or antibody sensitization (immobilization) is easy, they are relatively inexpensive, and they are easily controllable in the polymerization reaction (PTL 1, etc.). In the case where polystyrene-based latex particles are used as the carrier in the latex turbidimetric immunoassay, however, when the concentration of a test substance in a test sample is dilute, the number of aggregates to be formed is small, and the apparent particle sizes of the aggregates are also small, as compared with the case where the concentration of the test substance with respect to the number of latex particles falls within an appropriate range, resulting in a disadvantageously insufficient sensitivity.

CITATION LIST

Patent Literature

PTL 1: WO 2003-005031
PTL 2: JP-A-2008-215816
PTL 3: JP-A-2001-296299
PTL 4: WO 2012-133771

SUMMARY OF INVENTION

Technical Problem

There are two major methods of increasing sensitivity. (1) A first method is to increase the particle size of latex particles. When the particle size is large, the absorption coefficient is large so that a difference in the aggregation change is easily detected even at a dilute concentration. (2) A second method is to increase the refractive index of latex particles, and consequently, to increase the absorption coefficient. When latex particles have the same particle size, a latex particle having a higher refractive index has a higher absorption coefficient, and therefore, detection sensitivity can be maintained even under a more dilute environment.

However, with regard to (1), if the particle size of the latex particles becomes too large, the latex particles precipitate during measurement or settle to the bottom of a storage bottle during storage, and thus there is a problem that measurement errors are increased or storage stability is remarkably deteriorated.

In order to improve this problem, PTL 2 suggests a method of using latex particles having a single-hole hollow structure. However, although the precipitation problem is solved, a decrease in the absorption coefficient caused by the single-hole hollow structure lowers detection sensitivity, and thus substantial improvement in the sensitivity cannot be achieved. With regard to (2), for example, PTL 3 and PTL 4 suggest a method of improving sensitivity by using latex particles composed of a material having a high refractive index. However, since the material having a high refractive index generally has a large specific gravity and the weight of particles becomes heavy, only particles having a particle size of less than 300 nm can be practically used as a reagent, and there is a limit to sensitivity improvement.

An object of the present invention is to provide latex particles for measurement reagents that enable high-sensitivity measurement even when measuring a test sample containing a test substance at a dilute concentration.

Solution to Problem

The present inventors have conducted intensive studies, and as a result, they found that precipitation of particles is suppressed by decreasing the specific gravity of latex particles containing a compound having a refractive index of 1.6 or more. Based on this finding, it was found to obtain latex particles for measurement reagents that enable high-sensitivity measurement even when measuring a test sample containing a test substance at a dilute concentration by greatly improving absorbance using particles in the range of large particle size which have not been practically used as a traditional reagent, thereby completing the present invention.

The present invention is as follows.

[1] Latex particles for measurement reagents having a coefficient of variation in particle diameters of 10% or less and an average particle diameter of 250 nm to 1000 nm, wherein the latex particles each contain 20% by weight or more of a compound having a refractive index of 1.60 or more, and the depth of a supernatant is 5 mm or less when a liquid dispersion having a solid matter concentration of 1% by weight, which is prepared by dispersing the latex particles in ultrapure water, is placed in a 10-ml measuring cylinder having a body inner diameter of 10.8 mm and is then allowed to leave for 10 days.

[2] The latex particles for measurement reagents of [1], wherein the compound having a refractive index of 1.60 or more includes a compound having at least one skeleton selected from the group consisting of a fluorene skeleton, a dinaphthothiophene skeleton, a naphthalene skeleton, an anthracene skeleton, a phenanthrene skeleton, and a carbazole skeleton.

[3] The latex particles for measurement reagents of [2], wherein the compound having a refractive index of 1.60 or more is a polymerizable compound.

[4] The latex particles for measurement reagents of any one of [1] to [3], wherein the compound having a refractive index of 1.60 or more is a polymer of a polymerizable compound.

[5] The latex particles for measurement reagents of any one of [1] to [4], wherein the latex particles contain 10% by weight or more of a polyfunctional polymerizable compound having at least one skeleton selected from the group consisting of a phenyl skeleton, a naphthalene skeleton, a fluorene skeleton, a dinaphthothiophene skeleton, an anthracene skeleton, a phenanthrene skeleton, and a carbazole skeleton.

[6] The latex particles for measurement reagents of any one of [1] to [5], wherein a specific gravity of a dry powder of the latex particles is less than 1.17 g/cm³.

[7] The latex particles for measurement reagents of any one of [1] to [6], wherein the latex particles do not show absorbance lower by over 5% than the value represented by the following formula (1):

Absorbance=3.28×particle diameter(μm)−0.28    Formula (1)

[8] Sensitized latex particles, wherein a substance to be specifically bonded to a test substance is supported on the latex particles for measurement reagents of any one of [1] to [7].

[9] A measurement reagent for turbidimetric immunoassay, wherein the sensitized latex particles of [8] are dispersed in a buffer solution.

Advantageous Effects of Invention

According to the present invention, it is possible to provide latex particles for measurement reagents that enable high-sensitivity measurement even when measuring a test sample containing a test substance at a dilute concentration. The latex particles for the measuring reagents of the present invention have a lower specific gravity than traditional latex particles to suppress precipitation and to allow use of particles having a larger particle size, thereby improving the measurement sensitivity of the test substance at the dilute concentration.

DESCRIPTION OF EMBODIMENTS

Hereinafter, the present invention will be described with reference to embodiments, but the present invention is not limited to the following embodiments.

[Latex Particles for Measurement Reagents]

The present invention relates to latex particles for measurement reagents having a coefficient of variation (CV value) in particle diameters of 10% or less and an average particle diameter of 250 nm to 1000 nm and each including 20% by weight or more of a compound having a refractive index of 1.60 or more, wherein when a dispersion having a latex particle concentration of 1.0% by weight, which is prepared by dispersing the latex particles for measurement reagents in pure water, is placed in a 10-ml measuring cylinder having a body inner diameter of 10.8 mm and is then allowed to leave for 10 days, the depth of a supernatant is 5 mm or less. Further, "the depth of a supernatant is 5 mm or less" means that the depth of the supernatant is 0 mm to 5 mm, and describes the lower limit of the practical range of the sedimentation degree of the latex particles for measurement reagents. Further, the "supernatant" refers to a state in which turbidity is less than 5% when the original value is regarded as 100, which may be confirmed, for example, by measuring the supernatant collected by a pipette using a spectrophotometer (U-3900 manufactured by Hitachi, Ltd.). The "ultrapure water" refers to water having a non-resistivity of 18.2 MΩ·cm and a TOC value of 5 ppb or less. The "ultrapure water" can be obtained, for example, by means of Milli-Q Integral MT instrument (manufactured by Merck) which is an ultrapure water system directly connected with tap water.

[Particles]
[Polymer Latex]

One embodiment of the latex particles for measurement reagents of the present invention may include latex particles including at least a polymer of a polymerizable compound (hereinafter, referred to as "polymer") and a compound having a refractive index of 1.60 or more (hereinafter, referred to as "high refractive index compound").

[Polymer of Polymerizable Compound]

The polymer included in the latex particles for measurement reagents of the present invention is a polymer of one or two or more polymerizable compounds, and the polymer can be obtained by polymerization treatment, such as light irradiation or heating, of a composition containing the polymerizable compound.

The polymerizable compound is a compound containing one or more polymerizable functional groups in one molecule, and may be a monofunctional polymerizable compound containing one polymerizable functional group in one molecule or a polyfunctional polymerizable compound containing two or more polymerizable functional groups in one molecule. Further, the polymerizable compound may be a monomer or a multimer such as an oligomer or a prepolymer.

The polymerizable compound may be used alone or in combination of two or more in any ratio. Further, when two or more polymerizable compounds are used, the combination of two or more polymerizable compounds may be any one of a combination of two or more monofunctional polymerizable compounds, a combination of two or more polyfunctional polymerizable compounds, and a combination of one or more monofunctional polymerizable compounds and one or more polyfunctional polymerizable compounds.

A molecular weight of the polymer is, for example, 80 or more and 50,000 or less, but is not particularly limited. In the present invention and in the present specification, the molecular weight refers to a weight average molecular weight which is measured in terms of polystyrene by gel permeation chromatography (GPC). The weight average molecular weight described below is a value measured by the following measurement.

GPC apparatus: GPC system (manufactured by Shimadzu Corp.)
Column: K-804L (manufactured by shodex)
Eluent: tetrahydrofuran (THF)

[Polymerizable Functional Group]

The polymerizable functional group may be a radical polymerizable functional group, an ion polymerizable functional group, or a coordination polymerizable functional group, and preferably, a radical polymerizable functional group. From the viewpoint of the reactivity of the polymerization reaction, polymerizable groups such as an ethylenically unsaturated bond-containing group, an epoxy group, an oxetane group, and a methylol group may be mentioned. An ethylenically unsaturated bond-containing group is more preferred. The ethylenically unsaturated bond-containing group may include a (meth) acryloyloxy group, a (meth) acryloyl group, a vinyl group, a styryl group, and an allyl group, and more preferably, a (meth)acryloyl group, a vinyl group, and a styryl group. In the present invention and the present specification, the description of "(meth)acryloyl group" is used to mean at least one of an acryloyl group and a methacryloyl group. The same applies to "(meth)acryloyloxy group", "(meth)acrylate", "(meth) acrylic", etc. In the polyfunctional polymerizable compound, the number of polymerizable groups contained in the compound is two or more in one molecule.

Specific examples of the monofunctional polymerizable compound having the ethylenically unsaturated bond-containing group may include, but are not particularly limited to, as vinyl compounds, styrenic monomers, such as styrene, α-methylstyrene, chlorostyrene, etc.; naphthalene compounds such as 1-vinyl naphthalene, 2-vinyl naphthalene, etc.; anthracenyl compounds such as 2-vinyl anthracene, 9-vinyl anthracene, etc.; phenanthrene compounds such as 3-vinyl phenanthrene, 9-vinyl phenanthrene, etc.; dinaphthothiophene compounds such as 6-vinyl dinaphthothiophene, 6-vinyl ether dinaphthothiophene, etc.; carbazole compounds such as 9-vinyl carbazole, etc.; vinyl ether compounds such as methyl vinyl ether, ethyl vinyl ether, propyl vinyl ether, etc.; acid vinyl ester compounds such as vinyl acetate, vinyl butyrate, vinyl laurate, vinyl stearate, etc.; halogen-containing monomers such as vinyl chloride, vinyl fluoride, etc.; as (meth)acrylic compounds, aromatic (meth)acrylate compounds such as benzyl (meth)acrylate, etc.; polycyclic aromatic (meth)acrylate compounds such as methyl 2-(1-naphthyl) (meth)acrylate, phenantyl (meth) acrylate, 6-(meth)acryloyloxymethyl dinaphthothiophene, 6-(meth)acryloyloxyethyl dinaphthothiophene, etc.; alkyl (meth)acrylate compounds such as methyl (meth)acrylate, ethyl (meth)acrylate, propyl (meth)acrylate, butyl (meth) acrylate, 2-ethylhexyl (meth)acrylate, lauryl (meth)acrylate, cetyl (meth)acrylate, stearyl (meth)acrylate, cyclohexyl (meth)acrylate, isobornyl (meth)acrylate, etc.; oxygen atom-containing (meth)acrylate compounds such as 2-hydroxyethyl (meth)acrylate, glycerol (meth)acrylate, polyoxyethylene (meth)acrylate, glycidyl (meth)acrylate, etc.; nitrile-containing monomers such as (meth)acrylonitrile, etc.; halogen-containing (meth)acrylate compounds such as trifluoromethyl (meth)acrylate, pentafluoroethyl (meth)acrylate, etc.; as α-olefin compounds, olefin compounds such as diisobutylene, isobutylene, linealene, ethylene, propylene, etc.; and conjugated diene compounds such as isoprene, butadiene, etc.

Specific examples of the multifunctional polymerizable compound having the ethylenically unsaturated bond-containing group may include, but are not particularly limited to, as vinyl compounds, vinyl monomers such as divinylbenzene, 2,12-divinyldinaphthothiophene, 3,11-divinyldinaphthothiophene, 5,9-divinyldinaphthothiophene, 2,12-divinyloxymethyl dinaphthothiophene, 3,11-divinyl oxydinaphthothiophene, 1,4-divinyloxybutane, divinylsulfone, etc.; (meth)acrylic compounds, such as 2,12-di(meth)acryloyloxymethyl dinaphthothiophene, 3,11-di(meth)acryloyloxymethyl dinaphthothiophene, tetramethylolmethane tetra(meth)acrylate, tetramethylolmethane tri(meth)acrylate, tetramethylolmethane di(meth) acrylate, trimethylolpropane tri(meth)acrylate, dipentaerythritol hexa(meth)acrylate, dipentaerythritol penta(meth) acrylate, glycerol tri(meth)acrylate, glycerol di(meth) acrylate, (poly)ethylene glycol di(meth)acrylate, (poly) propylene glycol di(meth)acrylate, (poly)tetramethylene glycol di(meth)acrylate, 1,4-butanediol di(meth)acrylate, 9,9-bis(4-(meth)acryloyloxyphenyl)fluorene, 9,9-bis(4-(meth)acryloyloxymethoxyphenyl) fluorene, 9,9-bis(4-(2-(meth)acryloyloxyethoxy)phenyl) fluorene; allyl compounds such as triallyl(iso)cyanurate, triallyl trimellitate, diallyl phthalate, diallyl acrylamide, diallyl ether, 9,9'-bis (4-allyloxyphenyl) fluorene; as silicone compounds, silane alkoxide compounds such as tetramethoxysilane, tetraethoxysilane, methyltrimethoxysilane, methyltriethoxysilane, ethyltrimethoxysilane, ethyltriethoxysilane, isopropyltrimethoxysilane, isobutyltrimethoxysilane, cyclohexyl trimethoxysilane, n-hexyltrimethoxysilane, n-octyltriethoxysilane, n-decyltrimethoxysilane, phenyltrimethoxysilane, dimethyldimethoxysilane, dimethyldiethoxysilane, diisopropyldimethoxysilane, trimethoxysilyl styrene, γ-(meth) acryloxypropyltrimethoxysilane, 1,3-divinyltetramethyldisiloxane, methylphenyldimethoxysilane, and diphenyldimethoxysilane, etc.; polymerizable double bond-containing silane alkoxide such as vinyltrimethoxysilane, vinyltriethoxysilane, dimethoxymethylvinylsilane, dimethoxyethylvinylsilane, diethoxymethylvinylsilane, diethoxyethylvinylsilane, ethylmethyldivinylsilane, methylvinyldimethoxysilane, ethylvinyldimethoxysilane, methylvinyldiethoxysilane, ethylvinyldiethoxysilane, p-styryltrimethoxysilane, 3-methacryloxypropylmethyldimethoxysilane, 3-methacryloxypropyl trimethoxy silane, 3-methacryloxypropylmethyldiethoxysilane, 3-methacryloxypropyl triethoxy silane, 3-acryloxypropyltrimethoxysilane, etc.; cyclic siloxanes such as decamethylcyclopentasiloxane, etc.; modified (reactive) silicone oils such as one-terminal silicone oil, both-terminal silicone oil, side-chain type silicone oil, etc.; and carboxyl group-containing monomers such as (meth)acrylic acid, maleic acid, and maleic anhydride, etc.

Among them, aromatic vinyl compounds such as styrene, divinylbenzene, etc.; polycyclic aromatic vinyl compounds such as vinyl naphthalene, vinyl anthracene, vinyl phenanthrene, vinyl dinaphthothiophene, vinyl carbazole, etc.; (meth)acrylic acid esters having an aromatic or polycyclic aromatic skeleton such as benzyl (meth)acrylate, fluorene di(meth)acrylate, naphthyl (meth) acrylate, phenantyl (meth)acrylate, etc. may be used, because they do not decrease the refractive index.

In the aromatic vinyl compounds and polycyclic aromatic vinyl compounds, substituents of the aromatic ring may include an alkyl group, a hydroxyl group, a carboxyl group, a halogen group (e.g., a fluorine group, a chlorine group, a bromine group, an iodine group), etc. Examples of the alkyl group may include a methyl group, an ethyl group, an n-propyl group, an i-propyl group, an n-butyl group, an i-butyl group, an s-butyl group, a t-butyl group, an n-pentyl group, a 1-methyl-n-butyl group, a 2-methyl-n-butyl group, a 3-methyl-n-butyl group, a 1,1-dimethyl-n-propyl group, a 1,2-dimethyl-n-propyl group, a 2,2-dimethyl-n-propyl group, a 1-ethyl-n-propyl group, an n-hexyl group, a 1-methyl-n-pentyl group, a 2-methyl-n-pentyl group, a 3-methyl-n-pentyl group, a 4-methyl-n-pentyl group, a 1,1-dimethyl-n-butyl group, a 1,2-dimethyl-n-butyl group, a 1,3-dimethyl-n-butyl group, a 2,2-dimethyl-n-butyl group, a 2,3-dimethyl-n-butyl group, a 3,3-dimethyl n-butyl group, a 1-ethyl-n-butyl group, a 2-ethyl-n-butyl group, a 1,1,2- trimethyl-n-propyl group, a 1,2,2-trimethyl-n-propyl group, a 1-ethyl-1-methyl-n-propyl group, a 1-ethyl-2-methyl-n-propyl, etc. Further, a cyclic alkyl group may be used as the alkyl group. For example, a C1-C10 cyclic alkyl group may include a cyclopropyl group, a cyclobutyl group, a 1-methyl-cyclopropyl group, a 2-methyl-cyclopropyl group, a cyclopentyl group, a 1-methyl-cyclobutyl group, a 2-methyl-cyclobutyl group, a 3-methyl-cyclobutyl group, a 1,2-dimethyl-cyclopropyl group, a 2,3-dimethyl-cyclopropyl group, a 1-ethyl-cyclopropyl group, a 2-ethyl-cyclopropyl group, a cyclohexyl group, a 1-methyl-cyclopentyl group, a 2-methyl-cyclopentyl group, a 3-methyl-cyclopentyl group, a 1-ethyl-cyclobutyl group, a 2-ethyl-cyclobutyl group, a 3-ethyl-cyclobutyl group, a 1,2-dimethyl-cyclobutyl group, a 1,3-dimethyl-cyclobutyl group, a 2,2-dimethyl-cyclobutyl group, a 2,3-dimethyl-cyclobutyl group, a 2,4-dimethyl-cyclobutyl group, a 3,3-dimethyl-cyclobutyl group, a 1-n-propyl-cyclopropyl group, a 2-n-propyl-cyclopropyl group, a 1-i-propyl-cyclopropyl group, a 2-i-propyl-cyclopropyl group, a 1,2,2-trimethyl-cyclopropyl group, a 1,2,3-trimethyl-cyclopropyl group, a 2,2,3-trimethyl-cyclopropyl group, a 1-ethyl-2-methyl-cyclopropyl group, a 2-ethyl-1-methyl-cyclopropyl group, a 2-ethyl-2-methyl-cyclopropyl group, a 2-ethyl-3-methyl-cyclopropyl group, etc.

[Compound Having Refractive Index of 1.60 or More]

The latex particles for measurement reagents of the present invention include a high refractive index compound (a compound having a refractive index of 1.60 or more). The high refractive index compound may be, but is not particularly limited to, preferably a compound having at least one skeleton selected from the group consisting of a fluorene skeleton, a dinaphthothiophene skeleton, a naphthalene skeleton, an anthracene skeleton, a phenanthrene skeleton, a pyrene skeleton, and a carbazole skeleton. A preferred combination of the skeletons may include a fluorene skeleton, a dinaphthothiophene skeleton, and a naphthalene skeleton.

Specific examples of the high refractive index compound may include fluorene, dinaphthothiophene, naphthalene, anthracene, phenanthrene, carbazole, etc. Among them, fluorene, dinaphthothiophene, and naphthalene are preferred.

When the high refractive index compound is a polymerizable compound having a polymerizable functional group, it may form a polymer by homopolymerization or may form a polymer by copolymerization with another polymerizable compound. Specific examples of the polymerizable compound may include naphthyl compounds such as 9,9-bis(4-(meth)acryloyloxyphenyl)fluorene, 9,9-bis(4-(meth)acryloyloxymethoxyphenyl)fluorene, 9,9-bis(4-(2-(meth)acryloyloxyethoxy)phenyl)fluorene, 6-vinyldinaphthothiophene, 6-vinyl ether dinaphthothiophene, 2,12-divinyl dinaphthothiophene, 3,11-divinyl dinaphthothiophene, 5,9-divinyl dinaphthothiophene, 2,12-divinyloxymethyl dinaphthothiophene, 3,11-divinyloxy dinaphthothiophene, 2,12-di(meth)acryloyloxymethyl dinaphthothiophene, 3,11-di(meth)acryloyloxymethyl dinaphthothiophene, 1-vinyl naphthalene, 2-vinyl naphthalene, divinyl naphthalene, naphthyl methacrylate, etc.; anthracenyl compounds such as 2-vinyl anthracene, 9-vinyl anthracene, etc.; vinyl phenanthrene; vinylpyrene, N-vinylcarbazole, etc. Among them, a compound having at least one skeleton selected from the group consisting of a fluorene skeleton, a dinaphthothiophene skeleton, and a naphthalene skeleton is preferred.

[Content of High Refractive Index Compound]

The high refractive index compound is preferably included in an amount of 20% by weight or more in the latex particle for measurement reagents. If the content is less than 20% by weight, it may not compensate for the decrease in absorbance due to hollow latex particles for measurement reagents described later, and sensitivity may be reduced. The content is more preferably 30% by weight or more, and much more preferably 50% by weight or more. The upper limit is, but not particularly limited to, 96% by weight or less.

[Porous Hollow Structure]

The latex particles for measurement reagents of the present invention has a porous hollow structure. Due to the porous hollow structure, the latex particles have a lower specific gravity than latex particles having no porous hollow structure.

The "porous" refers to having two or more hollow structures, more preferably five or more hollow structures, and much more preferably ten or more hollow structures, when observing the cross-section of a particle. The hollow structure may be a single hole or a continuous hole. The particles having the porous hollow structure can suppress precipitation to improve reagent reproducibility and can suppress the decrease in refractive index of the particle, as compared with a single-hole structure, thereby enabling high sensitivity measurement. The diameter of the pores in the porous hollow structure is preferably 100 nm or less, more preferably 50 nm or less, and much more preferably 10 nm or less.

The shape of the pores may include an uneven shape formed on the surface of the latex particles, a gap between polymer chains forming the latex particles, and a shape having both the former and the latter.

A method of confirming the porous hollow structure of the latex particles for measurement reagents may include an observation method using SEM (scanning electron microscope) or TEM (transmission electron microscope). When the pores are small and difficult to observe, the porous hollow structure can be confirmed, for example, by measuring the specific gravity of a dry powder described above. Further, in the case of the continuous holes, the specific surface area of the particles is large, and thus it is possible to confirm the porous hollow structure by measuring the BET specific surface area using, for example, "NOVA 4200e" manufactured by Quantachrome Instruments. In this case, the BET specific surface area is larger than the theoretical value of $6/\rho D$ ($\rho$: density, D: particle size), and preferably 1.5 times or more, more preferably 2 times or more, and much more preferably 5 times or more.

Another method of confirming the porous hollow structure may include a method of utilizing the feature of the latex particles for measurement reagents that the surface area is large due to the porous hollow structure. Specifically, the latex particles having the porous hollow structure are first immersed in a predetermined metal-based dye, and the residual metal weight obtained by firing the latex particles is measured. In addition, the residual metal weight is also measured for latex particles having the same average particle size as the above latex particles but having no porous structure. The presence of the porous hollow structure can be confirmed from a difference between the obtained residual metal weights of the latex particles.

Further, after dyeing the porous hollow structure portion of the latex particles for measurement reagents, the cross-section of the latex particles may be observed. Specifically, the latex particles for measurement reagents are immersed in a predetermined dye to stain the pores of the porous hollow structure, and then the particles are embedded in an epoxy resin. A cross-section of the particles is prepared using a cross section polisher (IB-19520CCP manufactured by JEOL), and observed by FE-SEM (S-4800, manufactured by Hitachi High-Technologies Corp.) equipped with a high sensitivity YAG backscattered electron detector.

In general, when latex particles having a small particle size settle to the bottom of a container containing a solvent or aggregate, the latex particles are closely packed with each other, and thus it is difficult to redisperse the latex particles even though stirring the solvent. However, in the case where the porous hollow structure is formed in the latex particles due to gaps between the polymer chains, the latex particles are loosely packed with each other due to a yarn spherical shape of the latex particles. Therefore, even when the latex particles having the porous hollow structure settle to the bottom of a container containing a solvent or aggregate, the latex particles can be easily redispersed by stirring the solvent.

[Crosslinking Material]

The latex particles for measurement reagents of the present invention may preferably include a crosslinking material to facilitate maintenance of the porous structure. The crosslinking material is preferably a polyfunctional polymerizable compound.

The polyfunctional polymerizable compound is not particularly limited, and the above-described compounds may be used. Those having an aromatic skeleton or a polycyclic aromatic skeleton are preferred because they do not reduce the refractive index. Among them, those having at least one skeleton selected from the group consisting of a phenyl skeleton, a naphthalene skeleton, a fluorene skeleton, a dinaphthothiophene skeleton, an anthracene skeleton, a phenanthrene skeleton, a pyrene skeleton, and a carbazole skeleton are more preferred.

The polyfunctional polymerizable compounds may include divinylbenzene, divinylnaphthalene, 9,9-bis(4-(meth)acryloyloxyphenyl)fluorene, 9,9-bis(4-(meth)acryloyloxymethoxyphenyl)fluorine, 9,9-bis(4-(2-(meth)acryloyloxyethoxy)phenyl)fluorene, 2,12-divinyl dinaphthothiophene, 3,11-divinyl dinaphthothiophene, 5,9-divinyl dinaphthothiophene, 2,12-divinyloxymethyl dinaphthothiophene, 3,11-divinyloxy dinaphthothiophene, 2,12-di(meth)acryloyloxymethyl dinaphthothiophene, 3,11-di(meth)acryloyloxymethyl dinaphthothiophene, etc.

The latex particles preferably contain a homopolymer of the polyfunctional polymerizable compound or a copolymer with another polymerizable monomer. In the case of the copolymer with another polymerizable monomer, the polyfunctional polymerizable compound is preferably 5% by weight or more, and more preferably 10% by weight or more from the viewpoint of facilitating maintenance of the porous structure.

[Preparation Method]

A method of preparing the latex particles for measurement reagents of the present invention is not particularly limited, and an emulsion polymerization method, a mini-emulsion polymerization method, a suspension polymerization method, a microsuspension polymerization method, a soap-free polymerization method, a seed method, a solvent evaporation method, a phase transition emulsification method, and combinations thereof are used.

More specifically, a preferred method of including 20% by weight or more of the high refractive index compound may include (1) a method including the steps of mixing a polymerizable compound, a high refractive index compound, a polymerization initiator, and a hydrophobic solvent capable of dissolving both of the polymerizable compound and the high refractive index compound to prepare a polymerizable compound solution; adding the polymerizable compound solution to an aqueous solution in which a surfactant and a dispersion stabilizer are dissolved to form droplets by emulsification, transfer emulsification, suspension, etc.; polymerizing the polymerizable compound by heating, etc.; distilling off the hydrophobic solvent; and equalizing the particle size by filtration, classification, etc. [an emulsification, suspension polymerization method], (2) a method including the steps of dissolving both a polymer and a high refractive index compound in a hydrophobic solvent capable of solubilizing both of them to prepare a hydrophobic solution; forming droplets of the hydrophobic solution in an aqueous solution in which a surfactant and a dispersion stabilizer are dissolved; distilling off the hydrophobic solvent; and equalizing the particle size by filtration, classification, etc. [a solvent evaporation method], (3) a method including the steps of dispersing particles (hereinafter, also referred to as "seed particles") made of a polymer of a monofunctional polymerizable monomer as a template in water in which a surfactant and/or a dispersion stabilizer are/is dissolved; and adding a hydrophobic solution in which a high refractive index compound is dissolved in a hydrophobic solvent capable of solubilizing both the seed particles and the high refractive index compound; absorbing the high refractive index compound together with the hydrophobic solvent into the particles; and distilling off the hydrophobic solvent [a seed swelling method], and (4) a method including the steps of dispersing seed particles in water in which a surfactant and/or a dispersion stabilizer are/is dissolved; adding a hydrophobic solution, in which a high refractive index compound, a polymerizable compound, and a polymerization initiator are dissolved in a hydrophobic solvent capable of solubilizing both the seed particles and the high refractive index compound; absorbing the high refractive index compound, the polymerizable compound and the polymerization initiator together with the hydrophobic solvent into the seed particles; polymerizing the polymerizable compound by heating etc.; and distilling off the hydrophobic solvent [a seed swelling polymerization method]

The methods of (3) and (4) are preferably used, because the particle size of the obtained latex particles for measurement reagents may be made uniform and the content of the high refractive index compound may be made uniform by using particles having a uniform particle size as seed particles. Furthermore, the method of (4) is more preferably used, because the porous structure is easily formed.

[Hydrophobic Solvent]

The hydrophobic solvent used in the methods of (1), (2), (3), and (4) is not particularly limited as long as it is a hydrophobic solvent capable of solubilizing the seed particles or the polymerizable compound and the high refractive index compound. However, it is preferable that its solubility parameter (SP value) is 10 or less and its boiling point is lower than that of water in order to distill off the hydrophobic solvent later.

Specifically, ethyl acetate (SP value: 9.1, boiling point: 77.1° C.), benzene (SP value: 9.2, boiling point: 80.1° C.), diisopropyl ether (SP value: 6.9, boiling point: 69° C.), chloroform (SP value: 9.1, boiling point: 61.2° C.), etc. may be used. These may be used alone or in combination of two or more thereof. Among them, ethyl acetate is preferred.

The SP value refers to a solubility parameter $\delta$ calculated from formula (A) shown below, using Okitsu's $\Delta F$ and $\Delta v$ values for various atomic groups (Okitsu Toshinao, "Adhesion", Journal of Polymer, Vol. 40, No. 8 (1996) p 342-350). In the case of mixtures and copolymers, the SP value refers to a solubility parameter $\delta_{mix}$ calculated from formula (B) shown below.

$$\delta = \Sigma\Delta F / \Sigma\Delta v \tag{A}$$

$$\delta_{mix} = \phi_1\delta_1 + \phi_2\delta_2 + \ldots \phi_n\delta_n \tag{B}$$

In these formula, $\Delta F$ represents Okitsu's $\Delta F$ for various atomic groups and $\Delta v$ represents the molar volume $\Delta v$. $\phi$ represents the volume fraction or molar fraction, with $\phi_1 + \phi_2 + \ldots \phi_n = 1$.

The hydrophobic solvent is not particularly limited, and in addition to the above compounds, for example, dodecane, decane, isododecane, nonane, n-hexyl ether, octane, isooctane, cyclooctane, diphenyl ether, hexane, propylbenzene, o-dichlorobenzene, ethyl benzene, p-xylene, toluene, diethyl ether, butyl acetate, carbon tetrachloride, methylene chloride, cyclohexane, heptane, etc. The hydrophobic solvent swells the particles and acts as a bulking agent. The hydrophobic solvent does not participate in the polymerization, and may be removed by a solvent evaporation method after polymerization. In this case, cyclohexane having a boiling point of 100° C. or lower is preferred. Further, in the case where it is retained as it is in the particles without being removed, decane and heptane which have a low solubility in water and a low specific gravity are preferred.

[Seed Particles]

The polymer constituting the seed particles is not particularly limited as long as it is a polymer of a monofunctional polymerizable compound, and the above-mentioned compounds may be used as a monofunctional polymerizable compound. From the viewpoint of maintaining the refractive index of the latex particles as much as possible, the monofunctional polymerizable compound is preferably a polymer composed of one or two or more of styrene, 1-vinyl naphthalene, and benzyl (meth)acrylate.

As a method of preparing the seed particles, known methods such as emulsion polymerization, mini-emulsion polymerization, suspension polymerization, microsuspension polymerization, soap-free polymerization, dispersion polymerization, etc. may be used. Among them, soap-free polymerization which is excellent in particle size controllability is preferably used.

Water-soluble persulfates, peroxides, and azo compounds are used as a polymerizable initiator used in the soap-free polymerization. Specifically, potassium persulfate, ammonium persulfate, 2,2'-azobis[2-(2-imidazolin-2-yl)propane], 2,2'-azobis(2-methylpropionamidine), 2,2'-azobis[N-(2-carboxyethyl)-2-methylpropionamidine], 2,2'-azobis[2-methyl-N-(2-hydroxyethyl)propionamide], 4,4'-azobis(4-cyanovaleric acid), cumene hydroperoxide, and t-butyl hydroperoxide may be exemplified.

Further, the molecular weight of the seed particles is preferably, for example, 80 or more and 50,000 or less, as described in the above "polymer of the polymerizable compound".

The particle size of the seed particles is preferably 10% to 93% of the desired particle size of the latex particles for measurement reagents. If the particle size is larger than 93%, the particles cannot include the required amounts of the high refractive index compound and the multifunctional polymerizable compound. If the particle size is smaller than 10%, the particles cannot absorb the predetermined amounts of high refractive index compound and the multifunctional polymerizable compound, and thus the desired particle size may not be obtained.

A method of preparing the seed particles is not particularly limited, and a known method may be used. However, a soap-free emulsion polymerization method without using an emulsifier (surfactant) is preferred. A polymerization initiator used in the emulsion polymerization method may include potassium persulfate, ammonium persulfate, etc., and preferably potassium persulfate. In the present invention, the particles can be prepared by introducing an ion exchange water, for example, a monomer and a polymerization initiator into a reaction vessel, replacing nitrogen in the reaction vessel under stirring, and performing a reaction at 65° C. to 80° C. for 12 hours to 42 hours. The obtained particles have a low CV value and excellent dispersion stability.

[Seed Polymerization Initiator]

The polymerization initiator used in the preparation methods of (1) and (4) is not particularly limited as long as it is a water insoluble initiator that can be dissolved in the hydrophobic solvent. Specifically, the polymerization initiator may include peroxides such as benzoyl peroxide, cumylperoxy neodecanoate, di-tert-butylperoxyhexahydroterephthalate, tert-butylperoxy pivalate, 1,1,3,3-tetramethylbutyl peroxy 2-ethylhexanoate, tert-butylperoxyisopropylcarbonate, di-2-ethylhexylperoxydicarbonate, di-α-cumylperoxide, tert-butylperoxybenzoate, tert-butyl-α-cumylperoxide, di-tert-butyl peroxide, 2,5-dimethyl-2,5-di(tert-butylperoxy) hexane, 2,5-dimethyl-2,5-di(tert-butylperoxy) hexyne-3,4, 4-di-tert-butylperoxy-oxyvalerate n-butyl ester, 1,1-bis(tert-butylperoxy)cyclohexane, tert-butylperoxyneodecanoate, t-butylperoxydiethyl acetate, bis (3,5,5-trimethylhexanoyl) peroxide, tert-butylperoxy-3,5,5-trimethylhexanoate, tert-butylperoxy 2-ethylhexyl carbonate, tert-butylperoxyneoheptanoate, 2,2-di-tert-butylperoxybutane, bis(tert-butyldioxyisopropyl)benzene, di-(4-tert-butylcyclohexyl) peroxydicarbonate, dibenzoyl peroxide, lauroyl peroxide, methyl ethyl ketone peroxide, etc., azo compounds such as 2,2'-azobis(isobutyronitrile), 2,2'-azobis(4-methoxy-2,4-dimethylvaleronitrile), 2,2'-azobis(2,4-dimethylvaleronitrile), 2,2'-azobis(methyl isobutyrate), 2,2'-azobis(2-methylbutyronitrile), 1,1'-azobis(cyclohexane-1-carbonitrile), dimethyl 2,2'-azobis(2-methylpropionate), etc., and preferably benzoyl peroxide.

[Average Particle Diameter of Latex Particles for Measurement Reagents]

The average particle diameter of the latex particles for measurement reagents of the present invention may be appropriately selected according to a specific method of latex turbidimetric immunoassay, the specification of measurement instrument used, etc., but the preferable lower limit is 0.25 μm (250 nm), and the preferable upper limit is 1 μm (1000 nm).

If the average particle diameter is 0.25 μm or less, the amount of optical change caused by aggregation is too small to obtain the sensitivity required for measurement. If the average particle diameter is more than 1 μm and a concentration of a test substance in the measurement reagent is high, the optical change caused by aggregation of the sensitized latex particles may be beyond a measurable range of an optical measuring device, and therefore, the optical change corresponding to the amount of the test substance may not be obtained. The "particle diameter" is an average particle diameter value of a volume statistic value which is measured using a particle size analyzer LS 13 320 manufactured by Beckman Coulter, Inc. The lower limit and the upper limit are respectively more preferably 0.3 µm (300 nm) and 0.8 µm (800 nm), and much more preferably 0.35 µm (350 nm) and 0.6 µm (600 nm).

A coefficient of variation (CV value) of the particle diameter of the latex particles for measurement reagents of the present invention is not particularly limited, and may be appropriately selected according to a specific method of latex turbidimetric immunoassay, the specification of measurement instrument used, etc., but preferably 10% or less. If the CV value exceeds 10%, production reproducibility in preparing sensitized latex particles may be lowered to degrade the performance (reproducibility) of a resulting measurement reagent. Further, the coefficient of variation of the particle diameter is calculated for 500 particles obtained from a transmission electron microscope (TEM) image in accordance with the following equation (1):

Coefficient of variation (CV value) of particle diameter=(standard deviation of particle diameter)/(average particle diameter)   Equation (1):

With regard to the latex particles, the specific gravity of the dry powder is preferably less than $1.17 \text{ g/cm}^3$. The lower limit is not particularly limited, but is about $1.01 \text{ g/cm}^3$. The specific gravity is more preferably $1.05 \text{ g/cm}^3$ to $1.15 \text{ g/cm}^3$. The "specific gravity" refers to a value that is measured using a true specific gravity meter (e.g., Accupyc II 1340 manufactured by Shimadzu Corp.).

Figure 1:
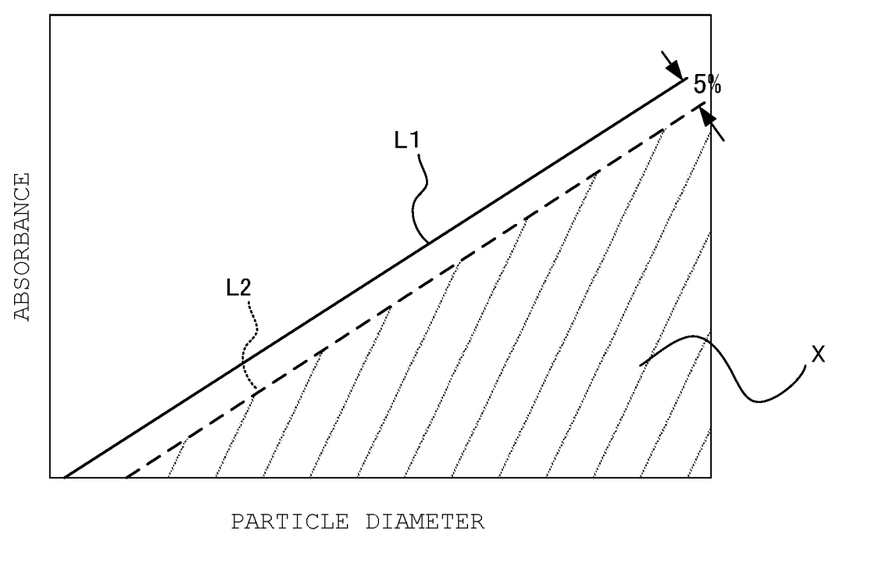
FIG. 1 is a conceptual diagram for the significance of absorbance.

It is preferable that the latex particles do not show absorbance lower by over 5% than the value represented by the following formula (1):

Absorbance=3.28×Particle diameter(µm)−0.28   Formula (1):

As shown in FIG. 1, "do not show absorbance lower by over 5%" means that when the particle diameter is taken on the horizontal axis and the absorbance is taken on the vertical axis, and formula (1) is represented by the solid line L1 and the lower boundary of 5% lower from L1 is represented by the dashed line L2, as shown in FIG. 1, the diagonal area X below L2 is removed.

[Sensitized Latex Particles/Measurement Reagent for Turbidimetric Immunoassay]

The latex particles for measurement reagents of the present invention are used as a carrier for supporting a substance to be specifically bonded to a test substance, thereby preparing sensitized latex particles. The sensitized latex particles including the latex particles for measurement reagents of the present invention supporting a substance to be specifically bonded to a test substance is also another aspect of the present invention. The sensitized latex particles are preferably dispersed in a buffer solution.

The substance to be specifically bonded to a test substance is not particularly limited as long as it is a physiologically active substance usually used as a reagent for immunoserologic tests (those used in an immunological aggregation reaction or aggregation inhibition reaction) or used in biochemical measurement. Among them, a substance usable in an antigen-antibody reaction is preferred.

Examples of the substance usable in an antigen-antibody reaction of the present invention may include antigens or antibodies of proteins, nucleic acids, nucleoproteins, hormones such as estrogen, lipids or the like. Examples of the antigen may include various antigens, receptors, enzymes or the like. More specific examples may include β2 microglobulin, C-reactive protein (CRP), human fibrinogen, ferritin, a rheumatoid factor (RA), α-fetoprotein (AFP), a mycoplasma antigen, an HBs antigen or the like. Examples of the antibody may include antibodies against various toxins, bacteria or the like. More specific examples may include an anti-streptolysin O antibody, an antiestrogen antibody, a β2 microglobulin antibody, a Treponema pallidum antibody, an antibody against syphilis lipid antigen, an anti-HBs antibody, an anti-HBc antibody, an anti-Hbe antibody, an anti-PSA antibody, an anti-CRP antibody or the like.

Further, the antibody to be supported on the latex particles for measurement reagents for preparing the sensitized latex particles may be not only an immunoglobulin molecule itself but also a fragment such as $F(ab')_2$. Furthermore, the antibody may be either a polyclonal antibody or a monoclonal antibody. The antibody can be obtained by a generally employed method. The terms "antigen-antibody reaction", "antigen" and "antibody" used herein have the general meanings as well as may include, in some cases, the aforementioned concept and form that sensitized latex particles may be aggregated through a specific binding reaction, and hence, these terms are not to be restrictively understood.

A method of preparing the sensitized latex particles by allowing the latex particles for measurement reagents of the present invention to support a substance to be specifically bonded to a test substance is not particularly limited, and any of traditionally known supporting methods via physical and/or chemical bond may be employed. The amount of a substance to be specifically bonded to a test substance to be supported on the sensitized latex particles of the present invention depends on the type of the substance to be specifically bonded to the test substance to be used, and may be experimentally set appropriately to an optimum amount.

Further, the terms "support", "sensitize", and "immobilize" used herein have the general meanings and are used in substantially the same meanings.

The sensitized latex particles of the present invention obtained in this manner are subjected to a coating (blocking) treatment with bovine serum albumin or the like, if necessary, and dispersed in an appropriate buffer solution to be used as a sensitized latex particle dispersion. The sensitized latex particle dispersion may be used as a measurement reagent for turbidimetric immunoassay. The measurement reagent for turbidimetric immunoassay in which the sensitized latex particles of the present invention are dispersed in a buffer solution is also another aspect of the present invention. The measurement reagent for turbidimetric immunoassay of the present invention may be combined with a diluent (a buffer solution) and a standard substance used for measurement to be used as a measurement reagent kit.

The diluent is used for diluting a measurement sample or the like. As the diluent, any of buffer solutions of pH 5.0 to pH 9.0 may be used. Specific examples may include a phosphate buffer solution, a glycine buffer solution, a Tris buffer solution, a borate buffer solution, a citrate buffer solution, a Good's buffer solution, etc.

The measurement reagent and the diluent for turbidimetric immunoassay of the preset invention may include various sensitizers for the purpose of improving the measurement sensitivity and accelerating an antigen-antibody reaction. Examples of the sensitizers may include alkylated polysaccharides such as methyl cellulose, ethyl cellulose, etc., pullulan, polyvinylpyrrolidone, etc.

The measurement reagent and the diluent for turbidimetric immunoassay of the present invention may include a protein such as albumin (bovine serum albumin or egg albumin), casein, gelatin or a hydrolysate thereof, an amino acid, a surfactant or the like for the purpose of inhibiting a non-specific aggregation reaction caused by a substance other than a test substance present in a measurement sample or improving the stability of the measurement reagent.

When the measurement reagent for turbidimetric immunoassay of the present invention is used, the amount of a test substance contained in a measurement sample can be measured by optically measuring the degree of aggregation of sensitized latex particles caused through a reaction between the test substance contained in the measurement sample and a substance to be specifically bonded to the test substance supported on the sensitized latex particles. For the optical measurement, an optical device capable of detecting the intensity of scattered light, the intensity of transmitted light, absorbance or the like, or an optical device provided with a plurality of detection methods for these may be used. Typically, any of biochemical autoanalyzers widely used for clinical laboratory tests may be used.

As a method of optically measuring the degree of aggregation, any of traditionally known methods may be employed, and examples thereof may include nephelometry in which the formation of aggregation is detected by increase of the turbidity, a method in which the formation of aggregation is detected by change of a particle size distribution or an average particle diameter, and an integrating sphere turbidity method in which change of forward scattered light caused by the formation of aggregation is measured by using an integrating sphere for comparing with a ratio to the intensity of transmitted light. Furthermore, examples of the measuring method may include a rate test (rate assay) in which at least two measured values are obtained at different points of time so as to obtain the degree of aggregation on the basis of increment (an increase rate) of the measured value caused between these points of time, and an end point test (end point assay) in which one measured value is obtained at one point of time (a point of time regarded as an end point of a reaction in general) so as to obtain the degree of aggregation on the basis of the measured value. Among them, the end point test by the nephelometry is suitably employed because the measurement can be easily and rapidly performed. The terms "immunoturbidimetric" and "turbidimetric immunoassay" used herein connote all the aforementioned concepts and forms, and these terms are not to be restrictively understood.

OTHER EMBODIMENTS

In the above-described embodiment for carrying out the present invention, a description is made about the latex particles including at least the polymer of the polymerizable compound and the compound having a refractive index of 1.60 or more as an embodiment of the latex particles for measurement reagents. However, the present invention is not limited to the embodiment, and for example, the polymer may have a composition similar to that of the high refractive index compound. Specifically, the present invention includes the case where the seed particles (the polymer of polymerizable compound) and the swelling monomer contained in the seed particles (the compound having a refractive index of 1.60 or more) have the same composition in the seed swelling method or in the seed swelling polymerization method.

EXAMPLE

Hereinafter, the present invention will be described in detail with reference to Examples and Comparative Examples. However, the present invention is not intended to be limited thereby.

Example 1

Seed particles for latex particles for measurement reagents of the present invention were first prepared by a soap-free emulsion polymerization method. 1200 mL of ion-exchange water and 120 mL of 1-vinyl naphthalene as a monomer were added to a reaction vessel, followed by stirring, and then the inside of the reaction vessel was replaced with nitrogen. When the temperature inside the reaction vessel reached 70° C., 13 mL of 3% (w/v) aqueous potassium persulfate solution was added dropwise. 24 hours after adding dropwise 3% (w/v) aqueous potassium persulfate solution, the reaction was stopped, and filtration was performed to obtain a suspension of poly 1-vinyl naphthalene seed particles.

The seed particles obtained by the above soap-free emulsion polymerization method were used to prepare latex particles for measurement reagents of the present invention by seed swelling polymerization. 8.0 g of 1-vinyl naphthalene and 0.08 g of benzoyl peroxide were dissolved in 10 g of ethyl acetate and stirred at room temperature for 6 hours to obtain a solution.

The solution was mixed with 20 g of the above seed particle suspension, and stirred at room temperature for 24 hours to internalize the solution into the seed particles. Thereafter, heating under stirring was performed at 70° C. for 10 hours to perform polymerization of 1-vinyl naphthalene. Then, heating under stirring was performed at 90° C. for 10 hours, and ethyl acetate was subjected to solvent evaporation to prepare composite particles of 1-vinyl naphthalene. The resulting latex particles had an average particle diameter of 0.398 μm and a CV value of the particle diameter was 5.3%.

The particle diameter of the latex particles was obtained from an average particle diameter value of a volume statistic value which was measured using a particle size analyzer "LS 13 320" manufactured by Beckman Coulter, Inc., and the CV value was obtained by placing the latex particles on a collodion membrane according to a general method, photographing a particle image by a transmission electron microscope, and measuring 500 or more particles observed on the image.

Example 2

Seed particles were obtained in the same manner as in Example 1. 8.0 g of 1-vinyl naphthalene, 1.0 g of divinyl benzene, and 0.09 g of benzoyl peroxide were dissolved in 10 g of ethyl acetate, and stirred at room temperature for 6 hours to obtain a solution. This solution was mixed with 10 g of the seed particle suspension to obtain latex particles by seed swelling polymerization in the same manner as in Example 1. The resulting latex particles had an average particle diameter of 0.411 μm and a CV value of the particle diameter was 4.5%.

Example 3

Seed particles were obtained in the same manner as in Example 1. 2.0 g of 6-vinyl dinaphthothiophene, 3.0 g of divinyl benzene, and 0.05 g of benzoyl peroxide were dissolved in 10 g of ethyl acetate, and stirred at room temperature for 6 hours to obtain a solution. This solution was mixed with 50 g of the seed particle suspension to obtain latex particles by seed swelling polymerization in the same manner as in Example 1. The resulting latex particles had an average particle diameter of 0.420 µm and a CV value of the particle diameter was 6.0%.

Example 4

Seed particles were obtained in the same manner as in Example 1, except that styrene was used as the monomer. 5.0 g of 9,9-bis(4-(2-(meth)acryloyloxyethoxy)phenyl)fluorene (manufactured by Osaka Gas Chemical Co., Ltd., EA-0200) and 0.05 g of benzoyl peroxide were dissolved in 10 g of ethyl acetate and stirred at room temperature for 6 hours to prepare a solution. This solution was mixed with 50 g of the seed particle suspension to obtain latex particles by seed swelling polymerization in the same manner as in Example 1. The resulting latex particles had an average particle diameter of 0.436 µm and a CV value of the particle diameter was 6.1%.

Example 5

Seed particles were obtained in the same manner as in Example 1. 9.0 g of 6-vinyl dinaphthothiophene and 0.09 g of benzoyl peroxide were dissolved in 10 g of ethyl acetate, and stirred at room temperature for 6 hours to obtain a solution. This solution was mixed with 10 g of the seed particle suspension to obtain latex particles by seed swelling polymerization in the same manner as in Example 1. The resulting latex particles had an average particle diameter of 0.463 µm and a CV value of the particle diameter was 7.2%.

Example 6

Latex particles were obtained in the same manner as in Example 2, except that the particle size was adjusted. The resulting latex particles had an average particle diameter of 0.301 µm and a CV value of the particle diameter was 3.6%.

Example 7

Latex particles were obtained in the same manner as in Example 2, except that the particle size was adjusted. The resulting latex particles had an average particle diameter of 0.600 µm and a CV value of the particle diameter was 4.3%.

Comparative Example 1

Soap-free emulsion polymerization was performed for preparation. 1200 mL of ion-exchange water and 120 mL of 1-vinyl naphthalene as a monomer were added to a reaction vessel, followed by stirring, and then the inside of the reaction vessel was replaced with nitrogen. When the temperature inside the reaction vessel reached 70° C., 13 mL of 3% (w/v) aqueous potassium persulfate solution was added dropwise. 24 hours after adding dropwise 3% (w/v) aqueous potassium persulfate solution, the reaction was stopped, and filtration was performed to obtain a suspension of poly 1-vinyl naphthalene latex particles. The resulting latex particles had an average particle diameter of 0.404 µm and a CV value of the particle diameter was 4.9%.

This Comparative Example corresponds to latex particles described PTL 3 and PTL 4.

Comparative Example 2

Seed particles were obtained in the same manner as in Example 1, except that methyl methacrylate was used as the monomer. The resulting latex particles had an average particle diameter of 0.410 µm and a CV value of the particle diameter was 3.9%.

This Comparative Example corresponds to latex particles described PTL 2.

[Evaluation 1] Measurement of Specific Gravity of Latex Particles for Measurement Reagents The latex particles for measurement reagents obtained in Examples 1 to 4 and Comparative Examples 1 to 2 were heated and dried at 100° C. for 3 hours, respectively, and then pulverized in a mortar to obtain a dried powder, of which specific gravity was measured using a true specific gravity meter (e.g., Accupyc II 1340 manufactured by Shimadzu Corp.), and comparative evaluation was performed. The results are shown in Table 1.

[Evaluation 2] Measurement of Absorbance of Latex Particles for Measurement Reagents The latex particles for measurement reagents obtained in Examples 1 to 4 and Comparative Examples 1 to 2 were prepared at a concentration of 0.01% by weight, respectively, and the absorbance at a wavelength of 580 nm was measured using a spectrophotometer (U-3900 manufactured by Hitachi). It is known that absorbance of polystyrene particles at a wavelength of 580 nm can be generally calculated by the following formula (2) (corresponding to PTL 1).

$$\text{absorbance} = 2.72 \times \text{particle diameter}(\mu m) - 0.22 \quad \text{Formula (2):}$$

Further, when a composition ratio of 1-vinyl naphthalene and styrene in the high refractive index material is 20:80, it is known that it corresponds to the straight line of the following formula (1) (corresponding to PTL 3 and PTL 4).

$$\text{absorbance} = 3.28 \times \text{particle diameter}(\mu m) - 0.28 \quad \text{Formula (1):}$$

The present invention aims to obtain particles with high sensitivity (high absorbance). Therefore, the evaluation was made using the formula (2) as a reference. The value as high as +20% or more was evaluated as ○○, the value of +20 to −5% was evaluated as ○, and the value of −5% or less was evaluated as x. The results are shown in Tables 1 and 2.

[Evaluation 3] Measurement of Sedimentation Degree of Latex Particles for Measurement Reagents The latex particles for measurement reagents obtained in Examples 1 to 4 and Comparative Examples 1 to 2 were dispersed in ultrapure water (water quality: non-resistivity of 18.2 MΩ cm, TOC value of 5 ppb or less) to obtain a dispersion having a latex particle concentration of 1.0% by weight, respectively. Each dispersion was placed in a 10 ml cylindrical measuring cylinder (manufactured by SIBATA Scientific Co., Ltd., trade name: "measuring cylinder custom A with a common ground glass flat stopper 026580-10A"/ height: 190 mm, body outer diameter: 13.1 mm, body inner diameter: 10.8 mm, made of glass), and left at room temperature for 10 days. Then, the depth (sedimentation degree) of the supernatant was measured, and comparative evaluation was performed.

Evaluation (x: 6 or more, Δ: 5, ○: 3 to 4, ○○: 2, ○○○: 0 to 1)

The results are shown in Tables 1 and 2.

TABLE 1

| | Particle composition ratio (%) | | | | | | | |
|---|---|---|---|---|---|---|---|---|
| | Seed particles | | | Swelling monomer | | | | |
| | MMA | St | 1-VNp | St | 1-VNp | 6VDNpTh | EA-0200 | DVB |
| Example 1 | | | 20 | | 80 | | | |
| Example 2 | | | 10 | | 80 | | | 10 |
| Example 3 | | | 50 | | | 20 | | 30 |
| Example 4 | 50 | | | | | | 50 | |
| Example 5 | | | 10 | | | 90 | | |
| Example 6 | | | 10 | | 80 | | | 10 |
| Example 7 | | | 10 | | 80 | | | 10 |
| Comparative Example 1 | | | 100 | | | | | |
| Comparative Example 2 | 20 | | | 80 | | | | |

TABLE 2

| | Physical properties of particles | | | | | | |
|---|---|---|---|---|---|---|---|
| | Particle structure | Average particle diameter (nm) | Specific gravity (g/cm³) | Absorbance (%) | | Sedimentation degree (mm) | |
| | | | | Evaluation | Value | Evaluation | Value |
| Example 1 | Porous hollow | 398 | 1.148 | ○○ | 1.43 | ○ | 3 |
| Example 2 | Porous hollow | 411 | 1.12 | ○○ | 1.49 | ○○ | 2 |
| Example 3 | Porous hollow | 420 | 1.146 | ○○ | 1.55 | ○ | 3 |
| Example 4 | Porous hollow | 436 | 1.034 | ○ | 1.15 | ○○○ | 1 |
| Example 5 | Porous hollow | 463 | 1.161 | ○○ | 1.62 | Δ | 5 |
| Example 6 | Porous hollow | 301 | 1.121 | ○○ | 0.89 | ○○○ | 1 |
| Example 7 | Porous hollow | 600 | 1.119 | ○○ | 2.05 | ○ | 4 |
| Comparative Example 1 | Solid | 404 | 1.178 | ○○ | 1.45 | X | 6 |
| Comparative Example 2 | Single-hole hollow | 410 | 1.024 | X | 0.75 | ○○○ | 1 |

In Tables 1 and 2, as compared with the particles of Comparative Example 1, the particles of Example 1 showed the lowered specific gravity and improved sedimentation degree, and achieved a practical range of 3 mm or less. Because of the porous hollow structure, the particles of Example 1 achieved high sensitivity (high absorbance) without lowering the refractive index of the particles. In Example 2, it was confirmed that the effect of lowering the specific gravity was improved by the addition of the cross-linking agent. In the particles of Comparative Example 2, although the lowered specific gravity and improved sedimentation degree were observed, the refractive index was greatly reduced because the particles had a single-hole hollow structure, and sensitivity (absorbance) lower than that of general styrene particles was obtained.

From the above, it was confirmed that the latex particles for measurement reagents of the present invention may enhance measurement sensitivity by using a material having a high refractive index, and may lower the specific gravity and suppress sedimentation of particles by having the porous hollow structure, thereby enabling high-sensitivity measurement even when measuring a test sample containing a test substance at a dilute concentration.

The invention claimed is:

1. Latex particles for measurement reagents having a coefficient of variation in particle diameters of 10% or less and an average particle diameter of 250 nm to 1000 nm,
   wherein the latex particles each contain 20% by weight or more of a compound having a refractive index of 1.60 or more,
   the depth of a supernatant is 5 mm or less when a liquid dispersion having a solid matter concentration of 1% by weight, which is prepared by dispersing the latex particles in ultrapure water, is placed in a 10-ml measuring cylinder having a body inner diameter of 10.8 mm and is then left for 10 days,
   wherein the compound having a refractive index of 1.60 or more includes a compound having at least one skeleton selected from the group consisting of a fluorene skeleton, a dinaphthothiophene skeleton, a naphthalene skeleton, an anthracene skeleton and a phenanthrene skeleton,
   wherein the latex particles have a porous hollow structure having two or more hollow structures.

2. The latex particles for measurement reagents of claim 1, wherein the compound having a refractive index of 1.60 or more is a polymerizable compound.

3. The latex particles for measurement reagents of claim 1, wherein the compound having a refractive index of 1.60 or more is a polymer of a polymerizable compound.

4. The latex particles for measurement reagents of claim 1, wherein the latex particles contain 10% by weight or more of a polyfunctional polymerizable compound having at least one skeleton selected from the group consisting of a phenyl skeleton, a naphthalene skeleton, a fluorene skeleton, a dinaphthothiophene skeleton, an anthracene skeleton, a phenanthrene skeleton, and a carbazole skeleton.

5. The latex particles for measurement reagents of claim 1, wherein a specific gravity of a dry powder of the latex particles is less than 1.17 g/cm$^3$.

6. The latex particles for measurement reagents of claim 1, wherein the latex particles do not show absorbance lower by over 5% than the value represented by the following formula (1):

$$\text{Absorbance} = 3.28 \times \text{particle diameter}(\mu m) - 0.28 \quad \text{Formula (1):}$$

7. Sensitized latex particles, wherein a substance to be specifically bonded to a test substance is supported on the latex particles for measurement reagents of claim 1.

8. A measurement reagent for turbidimetric immunoassay, wherein the sensitized latex particles of claim 7 are dispersed in a buffer.

* * * * *